United States Patent

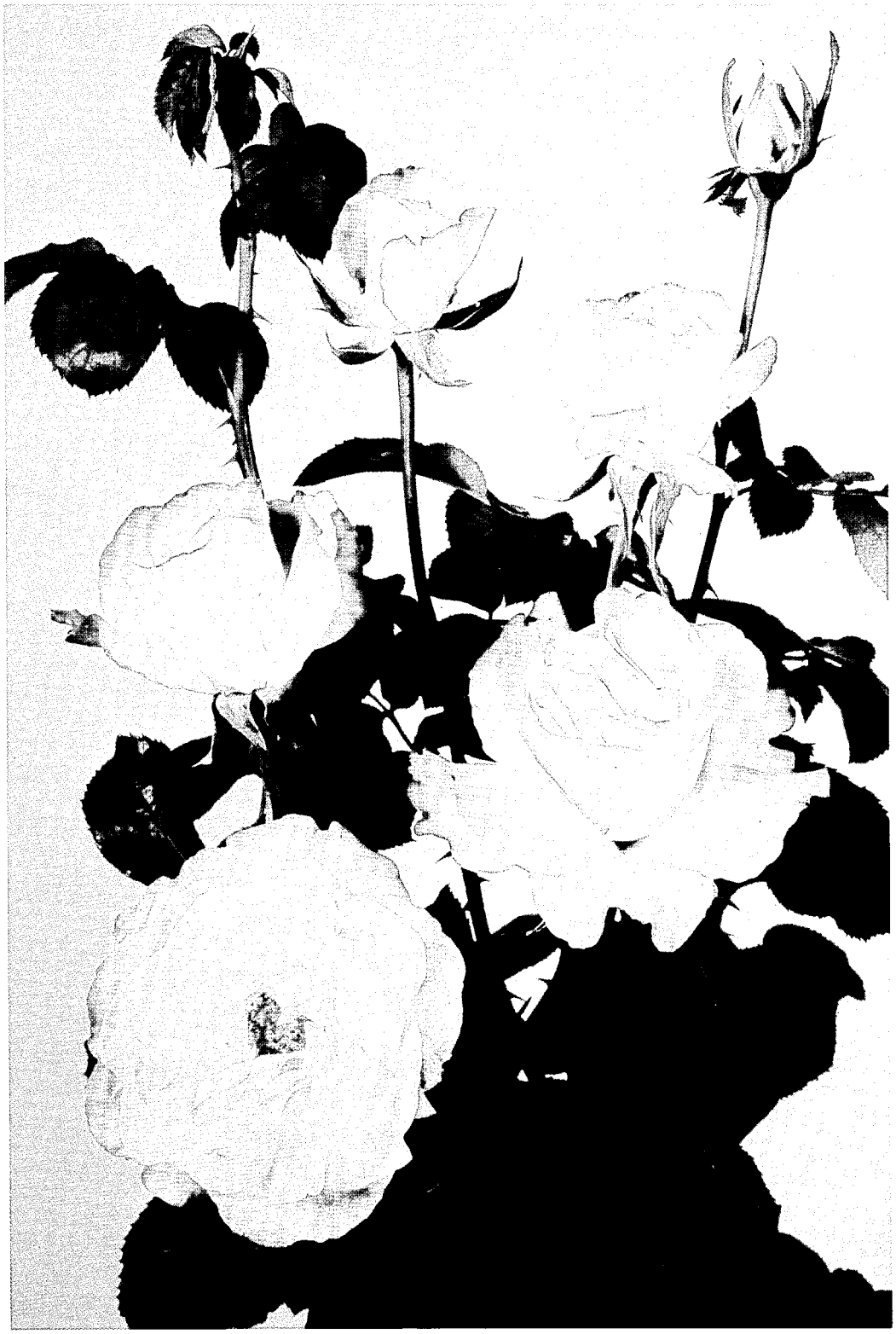

Plant Pat. 3,847

Patented Mar. 23, 1976

1

3,847

ROSE PLANT

Herbert C. Swim, Ontario, and Arnold W. Ellis, Bakersfield, Calif., assignors to Armstrong Nurseries, Inc., Ontario, Calif.

Filed Jan. 14, 1975, Ser. No. 540,856

Int. Cl. A01h 5/00

U.S. Cl. Plt.—11 1 Claim

ABSTRACT OF THE DISCLOSURE

A hybrid tea rose plant which bears moderately large blooms, usually singly, on medium-length stems. Change in coloration of the flower in response to light conditions is notable, ranging from creamy white to strong red in accordance with exposuse to light. The flower size may range up to 5½ inches with 35 to 45 petals and 6 to 15 petaloids. The fragrance is penetrating, fruity and strong.

This invention relates to a new class of hybrid tea rose. The plant is an outdoor bush seedling, best adapted for garden decoration. Its hardiness has not yet been evaluated.

It is a hybrid tea rose having Granada (Plant Pat. 2,214) as its seed parent, and Garden Party (Plant Pat. 1,814) for its pollen parent. It holds its distinguishing characteristics through succeeding propagations by budding.

It usually bears its flowers singly, but sometimes more, on normal medium-length stems, and it blooms almost continuously throughout the growing season. It has a strong fruity fragrance which is penetrating and pleasant.

The new variety differs in its petalage from its seed parent, Granada, and from its pollen parent, Garden Party, in that it normally shows 35 to 45 petals, plus from a half a dozen to about 15 petaloids, whereas Granada numbers from 18 to 25 petals, and Garden Party from 25 to 30 petals.

The flower color of Granada is described (see *Modern Roses 7*) as a "blend of rose, nasturtium-red and lemon yellow." In contrast, the flower color of this new cultivar is basically a creamy white which is overlaid, as exposed to sunlight, by pinks and reds, as will be described more fully hereinafter.

The flower coloration of the new cultivar differs likewise from that of its pollen parent, Garden Party, since the latter is a pale yellow to white, often tinged with light pink. The color difference is marked.

The new cultivar is somewhat larger than Granada, being 4½ to 5½ inches in diameter, whereas the flower size of the seed parent is more usually 4 to 5 inches in diameter. Visual observation indicates that the new variety consistently has larger blooms than its seed parent.

The fragrance of Garden Party is relatively slight, whereas the new variety has a very fragrant, strong and penetrating fruity perfume.

The accompanying drawing illustrates the plant in color and shows the flowering thereof from bud to full bloom.

Throughtout this specification, color names beginning with a small letter signify that the name of that color, as used in common speech, is aptly descriptive. Color names beginning with a capital letter designate values based upon the Nickerson Color Fan, put out by Munsell Color Corporation.

BUD

The peduncle is from average length to long, average in caliper, erect and stiff. It is smooth, but sometimes carries a few stipitate glands. Its color is near Moderate

2

Yellow Green, 2.5GY5/5, sometimes lightly overlaid with a color near Dark Red, 2.5R3/7, on the side of the peduncle which is exposed to sunlight.

Before the calyx breaks, the bud is medium in size, medium-length, pointed and ovoid. There are a few narrow foliaceous appendages on the surface of the bud, and usually slender foliaceous parts extending beyond the tip of the bud equal to one-half or more of its length.

As the calyx breaks, the color of the bud is near Brilliant Yellow Green, 2.5GY9/8, deeply overlaid where exposed to sunlight with a color between Strong Red, 5R4/12, and Dark Red, 2.5R4/10.

The inner surface of the sepals has a fine tomentum. The outer surface is smooth and without stipitate glands. Generally, of the five sepals, margins of two are lined with stipitate glands and a few narrow foliaceous parts; margins of two others are lined with a fine tomentum, while on the remaining sepal the margin on one side is lined with a fine tomentum and on the other side with stipitate glands.

As the first petal opens, the bud is average to large in size, medium-length to long, and urn-shaped. The outside surface of the first petal is between Moderate Red, 2.5R4/10, and Strong Red, 5R4/12, being near Brilliant Greenish Yellow, 10Y9/9, at the base. The inside surface is near Brilliant Yellow, 5Y9/9, at the base, blending through off-white and varying shades of pink to a color between Strong Red, 5R4/12, and Moderate Red, 2.5R4/10, where exposed to direct sunlight. The bud opens up well, and is not retarded or prevented from opening by cold, hot, wet, or dry weather.

BLOOM

When fully open, the bloom is from average to large, being from 4½ to 5½ inches in diameter. The petalage is from double to very double, with from 35 to 45 petals arranged regularly, plus 6 to 15 petaloids. At first the bloom is full and high centered, becoming open, full, and high centered. Inner petals are occasionally swirled in an irregular manner, but usually arranged in regular imbrication over other petals. The center may be visible or may be hidden by petaloids.

The petals are of medium thickness, with inside slightly shiny to satiny, the outside being satiny. The outside petals are nearly round to very broadly obovate, with apex somewhat irregular. The intermediate petals are broadly obovate. Inside petals are variable in shape, being broadly obovate to obovate, or irregular. The colors may be modified by being blotched, shaded and/or washed with other colors. Colors may vary with the temperature and the amount of exposure to sunlight.

The paragraphs immediately following describe color values observed in a flower newly opened in the month of October. The plant had been grown outdoors in Ontario, Calif.

The outer surface of the outside petal is near Brilliant Greenish Yellow, 7.5Y9/8, at the base, blending through off-white and varying shades of pink (mostly near Strong Purplish Red, 7.5RP5/12) to a color between Moderate Red, 2.5R4/10, and Strong Red, 5R4/12, where exposed to sunlight. The inner surface of the outside petal is essentially of the same coloration as the outer surface, except that the off-white area generally is greater on the inner surface because of shading and less exposure to sunlight.

The outer surface of the intermediate petal is essentially of the same coloration as the outside petal, except that there is a larger off-white area because of shading by other petals. The inner surface is the same as the outer surface.

On both the outer and inner surfaces of the inside petal, the color values are smilar to the outer surface of the outside petal if given sufficient exposure to direct sunlight. If given only slight exposure to sunlight, pink shades may show at the tips of the petals. If shaded, or without adequate exposure to sunlight, petal color is near Brilliant Greenish Yellow, 7.5Y9/8, at the base, blending to off-white throughout the petal.

The paragraphs immediately following describe the color values observed in a bloom which had been open for three days, outdoors, in the month of October. The plant had been grown outdoors, in Ontario, Calif.

The outer surface of the outside petal was near Brilliant Greenish Yellow, 10Y9/9, at the base, blending through off-white to varying degrees of Strong Purplish Red, 7.5RP4/11, which is deepest where exposed to direct sunlight. The inner surface of the outside petal was near Brilliant Greenish Yellow, 7.5Y9/9, at the base, blending through off-white to varying degrees of a color between Strong Red, 5R4/12, and Deep Purplish Red, 10RP3/10, toward the margins, the color being deepest where exposed to direct sunlight.

The outer surface of the inside petal was near Brilliant Yellow, 5Y9/9, at the base, blending through off-white to varying degrees of a color near Deep Purplish Pink, 58P6/10, toward the margins, the color being deepest where exposed to direct sunlight. The inner surface of the inside petal was the same as the outer surface, but generally with more uniform exposure to sunlight and thus, with more of the deeper tones.

It should be noted that the basic flower color is creamy white (off-white), but this color is remarkably masked by exposure to light, so that the petals are set off toward the outer margins by a color between Moderate Red, 2.5R4/10, and Strong Red, 5R4/12, giving a general color effect of contrasting red and white, as if the creamy white flower had been partially dipped in red paint.

After being three days open, the general color effect of the bloom is between Strong Purplish Red, 10R4/12, and Strong Purplish Red, 7.5RP5/12, but with prominent, contrasting areas of off-white coloration between the petals.

The petals drop off cleanly, except for the petaloids, and are affected by weather as follows: the flower color intensity and hue may vary with temperature and intensity of sunlight.

The flower on the bush in the garden persists attractively for from 4 to 5 days in the month of October, in the locality named. Cut roses grown outdoors and kept at living-room temperttures will last from 4 to 6 days in the month of October.

REPRODUCTIVE ORGANS

Stamens: The stamens are average in number, regularly arranged about the pistils.

Filaments: The filaments are of medium length, being from ¼ to 5/16 inch in length, and near Vivid Yellow, 5Y8/12, in color. Most are with anthers.

Anthers: The anthers are small, opening at various times. On both the upper and lower sides the color is near Brilliant Yellow, 2.5Y9/9, the color along the margins being near Moderate Orange Yellow, 10YR8/10.

Pollen: Pollen is sparse, and near Moderate Orange Yellow, 10YR8/10, in color.

Pistils: There are many pistils, approximately 160 in number.

Styles: Styles are uneven, average length, average caliper, an loosely bunched. Their color is near Brilliant Yellow Green, 2.5GY9/8.

Stigma: The stigma is near Brilliant Yellow, 2.5Y9/9, in color.

Ovaries: The ovaries mostly protrude from the calyx.

Hips: This cultivar has not set hips outdoors nor in the greenhouse at Ontario, Calif.: Under conditions here, it appears to be female-sterile.

FOLIAGE

The compound leaves usually comprise three to seven leaflets. These are from normal to abundant, medium in size, moderately heavy to somewhat leathery, in texture, and semi-glossy. The leaflets are broadly oval to broadly ovate, with apex mucronate and margin doubly to irregularly serrate.

The mature foliage displays upon its upper surface a coloration which is between Moderate Olive Green, 5GY4/3, and Grayish Olive Green, 5GY3/2. The under surface is a coloration not actually on the Nickerson Color Fan, but describable as a grayish light olive green.

The young foliage is between Moderate Yellow Green, 5GY5/6, and Moderate Olive Green, 5GY4/3, on its upper surface, this being lightly to heavily overlaid with near Dark Red, 2.5R3/7. Its under surface is near Deep Purplish Red, 10RP3/10, in its general color effect.

The rachis is average in size, grooved on its upper side, with some stipitate glands on the edges. Its under side is sparsely prickly.

The stipules are medium-length, narrow, and with medium-length narrow points turning out at an angle of more than 45°.

The plant displays an average resistance to mildew, when compared to other commercial varieties grown under similar conditions at Ontario, Calif.

GROWTH

The plant is of upright-spreading habit, bushy, and much branched, though not especially tall growing. It displays a very vigorous growth, with rapidly recycling bloom. The canes are of medium caliper.

The main stems are between Moderate Yellow Green, 2.5GY5/5, and Strong Yellow Green, 2.5GY6/8, in color. They bear several medium-length to long large prickles, hooked slightly downward, with medium-length, moderately narrow base. Their color is between gray and Moderate Brown, 5YR3/3. There are no small prickles, and no hairs.

The branches are near Moderate Yellow Green, 2.5GY5/5, in coloration. They carry several large prickles which are medium-length, hooked slightly downward, with medium-length, moderately narrow base. Their color is near Moderate Brown, 5YR3/3. There are very few small prickles, and their color is the same as the large prickles. There are no hairs.

New shoots are near Strong Yellow Green, 5GY6/8, in color, heavily overlaid with near Dark Red, 2.5R3/7. They bear several medium-length to long large prickles, hooked slightly downward, with medium-length to long narrow base. Their color is near Dark Red, 2.5R3/7. There are usually no small prickles, or very few; if any, the color is the same as the large prickles. There are no hairs.

We claim:

1. A new variety of hybrid tea rose plant of the bush type and of moderate height, substantially as herein illustrated and described, which plant is further characterized by a plurality of the following features, taken in combination, namely, the tendency to produce blooms, usually one to a stem, ranging up to about 5½ inches in diameter and having up to about 45 petals and up to 15 petaloids, the bloom having a strong penetrating somewhat fruity fragrance and being especially characterized by the manner in which the basic creamy white color of its petals tends to be overlaid with shades of red and pink, which deepen on exposure to the sunlight, said plant further exhibiting little if any tendency either to set hips or produce seeds in the area of Southern California where it was propagated.

No references cited.

ROBERT E. BAGWILL, Primary Examiner